(12) United States Patent
Deng et al.

(10) Patent No.: US 6,574,575 B2
(45) Date of Patent: Jun. 3, 2003

(54) METHOD FOR RAPID CALIBRATION OF BEVERAGE DISPENSING MACHINE

(75) Inventors: Keren Deng, Plano, TX (US); Dwight U. Bartholomew, Dallas, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 09/962,418

(22) Filed: Sep. 25, 2001

(65) Prior Publication Data

US 2003/0060994 A1 Mar. 27, 2003

(51) Int. Cl.$^7$ .......................... G01L 25/00; G01L 27/00
(52) U.S. Cl. ......................... 702/105; 702/100
(58) Field of Search .............................. 702/23, 24, 25, 702/85, 90, 99, 100, 103–105; 356/317, 73, 445; 137/3, 9, 93

(56) References Cited

U.S. PATENT DOCUMENTS 5,946,083 A * 8/1999 Melendez et al. ............ 356/73
6,191,847 B1 * 2/2001 Melendez et al. .......... 356/317
6,326,612 B1 * 12/2001 Elklind et al. ........... 422/82.05

* cited by examiner

*Primary Examiner*—Bryan Bui
(74) *Attorney, Agent, or Firm*—William B. Kempler; W. James Brady; Frederick J. Telecky, Jr.

(57) ABSTRACT

A rapid sensor calibration technique applied prior to each Sensor 9 measuring a beverage in which water (zero Brix), at same temperature as beverage, is drawn from a Water Supply 3 via Valve 6 and passed over the fixed optic Sensor 9 in order to reference out any sensor temperature changes or beverage temperature changes or sensor surface fouling by the dispensed beverage. This technique of continuous and multiple calibrations, provides an enhanced "beverage dispensing system" calibration beyond that achievable using known calibration methods associated with automatically sensing and controlling beverage quality for soft drinks from a fountain dispenser using, for example, water at a specific temperature to initially calibrate Sensor 9, or using a high quality beverage, from a bottle, for example, at a known Brix level to initially calibrate Sensor 9.

27 Claims, 1 Drawing Sheet

METHOD FOR RAPID CALIBRATION OF BEVERAGE DISPENSING MACHINE

BACKGROUND OF THE INVENTION

1. Field of the Invention

The present invention relates in general to sensor systems and more particularly, to a method for implementing rapid calibration of a beverage dispensing machine to ensure the quality of beverages such as soft drinks.

2. Description of the Prior Art

Without limiting the scope of the invention, the background set forth herein below is described in connection with sensing and controlling the quality of beverages such as soft drinks. It should be appreciated by one skilled in the art that the term beverages refers to a variety of fluids and other media, and that the principles of the present invention are applicable to a variety of media.

The dispensing of fountain beverages is presently generally accomplished using either premix systems in which a finished beverage is delivered to a proprietor from a bottler, and postmix systems in which flavored syrup is delivered to the proprietor and mixed with water at the point of delivery.

A premix system generally utilizes product containers filled with finished soft drinks that may be under carbon dioxide pressure. In these systems, the product is normally delivered to the consumer via a single orifice dispensing valve. Premix systems are also used in bottling plants that typically operate at extremely high flow rates. These systems are relatively expensive installations and are unsuitable for most typical restaurant settings.

A postmix system generally utilizes flavored syrup combined with carbonated or still water at a prescribed ratio and delivered through a dispensing valve at a fountain having passages for both syrup and water. The valve combines the syrup and water immediately before delivery into a cup on an individual serving basis. The valves are typically adjusted periodically to alter the mix ratio of the ingredients of the beverage.

In the restaurant industry, the valves that control the delivery of the beverage constituents are typically manually adjusted after a taste test of the finished beverage or a customer's complaint, for example. The decision to alter the composition of the beverage is a highly subjective one, and is typically based on the operator's subjective preference regarding the desired taste or sweetness of the beverage. In addition, the manual adjustment of the valves significantly lacks precision and accuracy. It is furthermore highly susceptible to human error, and is therefore inherently unreliable and inaccurate. The manual adjustments are also time-consuming and cumbersome.

Various attempts at maintaining a consistent ratio of the components of the beverages offered at a soft drink fountain dispenser have been made in the prior art. In one method, predetermined volumes of syrup and carbonated water are measured in a container called a Brixing cup. "Brix," as understood by those skilled in the art, is the percent concentration of sugar. Proper Brixing is determined by ratio marks on the Brixing cup.

The Brixing method must be periodically repeated in order to account for any long term changes in the pressures or viscosities of the dispensed fluid. Short term variations in flow rates during a single dispensing operation, or between individual dispensing operations, cannot be accounted for by periodic manual adjustments.

In another method, the rate of flow of the syrup and carbonated water are measured with flow meters. The flow rates are adjusted and operate at a prescribed ratio. A flexible flow washer may be positioned in a flow line, and variations in fluid flow rate cause the opening of the washer to become enlarged or constricted. This method is flawed in that it does not account for factors contributing to variations in the accuracy of the mix ratio, such as changes in fluid viscosity. This method also lacks any significant degree of accuracy and is therefore unreliable.

U.S. patent application Ser. No. 09/549,287, entitled System and Method for Sensing and Controlling Beverage Quality, filed Apr. 14, 2000 by Melendez et al., and assigned to the assignee of the present invention, discloses among other things, use of a surface plasmon resonance sensor to implement a closed loop monitor and control system to maintain precise control of the beverage constituent concentrations associated with a product dispensed from a beverage dispensing machine. In practice, the beverage temperature is not well controlled and can vary greatly (e.g., 3° C.–25° C.). When this occurs, both the beverage temperature and the sensor temperature change unpredictably during operation, greatly affecting the refractive index measurements associated with a surface plasmon resonance sensor. Further, natural products from the beverage can foul the sensing surface of the sensor such that the sensor will generate erroneous readings.

SUMMARY OF THE INVENTION

Any inaccuracy in the ratio of the beverage constituents dispensed from a beverage dispensing machine results in inconsistency and undesirable variations in the quality and taste of the beverages. For example, dispensers that have poor accuracy and reliability may dispense a beverage that is too sweet or not sweet enough, or a carbonated soda that is flat. Variations from the desired mix accuracy also result in uneconomical use of the syrup.

In practice, the beverage temperature from dispensing system is not well controlled. It can vary from near 3° C. to 25° C. The dispense pattern, i.e., dispense time, the time between each dispense, is also irregular. These limitations, among others, can cause the beverage and sensor temperatures to change unpredictably during operation, which affects the refractive index sensor measurements associated with measuring the beverage quality. For example, the temperature change of a fixed optic sensor such as a surface plasmon resonance sensor will greatly affect refractive index reading. There is no existing method to measure this temperature change and, even if such a method existed, corrected for temperature-change-induced sensor variability would be difficult. Also, the temperature of beverage on the fixed optic sensor such as a surface plasmon resonance sensor will also affect refractive index reading because the measured refractive index of the beverage varies with temperature. Additionally, when the sensor is exposed to beverage, the nature product in the beverage will contaminate (i.e., foul) the sensor surface. These limitations, among others, can generate erroneous readings.

A need has therefore arisen for a method of sensing and controlling the quality of beverages that overcomes the limitations in the prior art. A method that provides for rapid calibration of the fixed optical sensor, to more accurately monitor beverage quality, would have great advantages over the prior art.

The present invention, according to one embodiment, comprises a method of automatically sensing and controlling beverage quality dispensed from a beverage dispenser, comprising the steps of a) supplying a first fluid, wherein the flow of the first fluid is controlled by a first valve; b) supplying a second fluid; c) mixing the first fluid and the second fluid (this mixture is called "beverage"); d) calibrating a fixed optic sensor via passing a fluid with well-known properties, such as zero-Brix water, (dispensed by the beverage dispenser) onto the sensing surface of the fixed optic sensor; the zero-Brix water must be at the same temperature as the beverage; e) passing a sample of beverage onto the sensing surface of the fixed optic sensor subsequent to calibrating the fixed optic sensor; f) measuring one or more properties of the beverage; g) controlling the first valve based on the one or more properties to ensure proper beverage quality; h) repeating steps a–g to maintain a desired ratio of the fluids; and i) dispensing the mixture into a receptacle.

BRIEF DESCRIPTION OF THE DRAWINGS

Other aspects, features and advantages of the present invention will be readily appreciated as the invention becomes better understood by reference to the following detailed description when considered in connection with the accompanying drawing figures in which like reference numerals designate like parts throughout the figures thereof and wherein.

While the above-identified drawing figures set forth particular embodiments, other embodiments of the present invention are also contemplated, as noted in the discussion. In all cases, this disclosure presents illustrated embodiments of the present invention by way of representation and not limitation. Numerous other modifications and embodiments can be devised by those skilled in the art which fall within the scope and spirit of the principles of this invention.

DETAILED DESCRIPTION OF THE PREFERRED EMBODIMENTS

Figure 1:
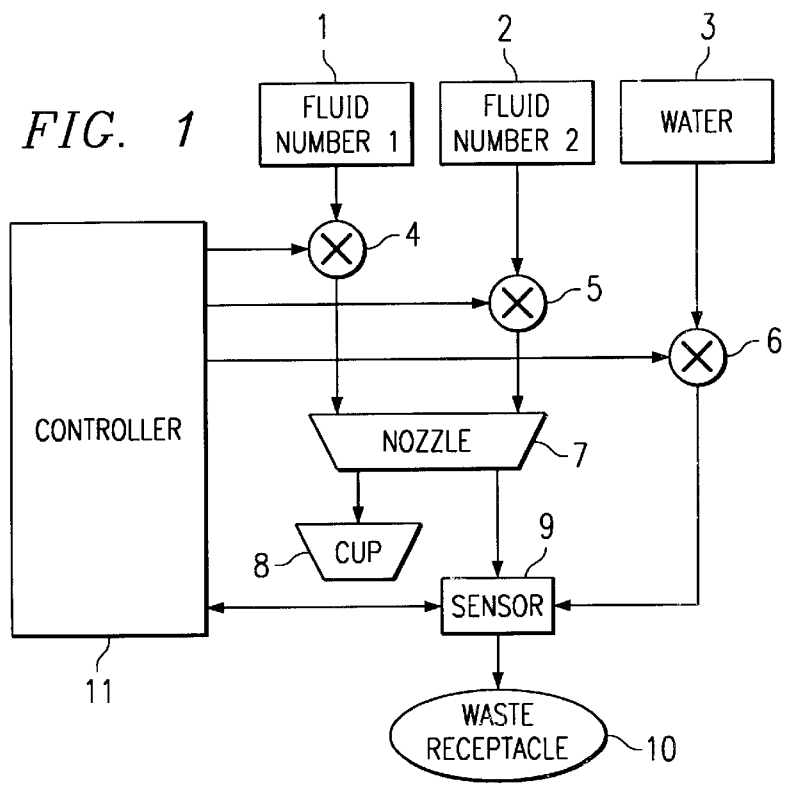
FIG. 1 depicts a block diagram of a system for sensing and controlling the quality of beverages where fluid #1 and fluid #2, when combined, form a beverage and fluid #3 is water.

Reference is now made to FIG. 1 which depicts a block diagram of a system for sensing and controlling the quality of a beverage which is the result of mixing two fluids.

The system of the present invention includes a controller 11 coupled with a plurality of electronically operated valves 4, 5, and 6 via electrical interfaces (not shown), as shown in FIG. 1. The system further includes a plurality of fluids 1 and 2, which are mixed in a nozzle 7 to produce a beverage that is distributed to Cup 8 for consumption. The system also includes a Water Supply 3 whose dispensing is controlled by an electronically operated Valve 6 via an electrical interface (not shown). The system may also comprise a refrigeration system (not shown) for keeping the fluids and water chilled, and an ice dispenser (not shown).

The Electronic Controller 11 may be a microcontroller or digital signal processing (DSP) unit, such as TMS320F206 or TMS320F243, manufactured by Texas Instruments Incorporated of Dallas, Tex.

Sensor 9 is a fixed optical sensor, such as a surface plasmon resonance sensor, which is capable of determining some property of fluids, beverages, or water. Beverage (or water) is directed onto the sensor surface, properties are measured, and the beverage is directed into a Waste Receptacle 10.

During operation, the Controller 11 is signaled to begin dispensing beverage. In one embodiment, the Controller 11 causes Valves 4 and 5 to open in such a way as to mix Fluids 1 and 2 in the dispensing Nozzle 7 in a set fashion (e.g., opening valve 4 while fluttering Valve 5). The resulting mixed beverage is dispensed into Cup 8 as well as a small portion is diverted onto Sensor 9. Sensor 9 measures the properties of the beverage and communicates these properties to Controller 11. Controller 11 retains the beverage properties. Immediately following this dispensing, Controller 11 closes valves 4 and 5. Then Controller 11 opens Valve 6 which causes Water 3 to flow onto Sensor 9; the properties of the water are measured and communicated to Controller 11. Then Controller 11 closes Valve 6. Controller 11 uses the water properties to provide a current calibration of the response of Sensor 9 to fluid properties. The Controller 11 recalibrates Sensor 9 and adjusts the previous beverage measurement (which was retained by Controller 11) to determine the true quality of the beverage. The true quality of the beverage can be a) Sent to a data storage device (not shown) to inspection at a later time.
b) Used by the Controller 11 to adjust the dispensing of Fluids 1 and 2 during the next dispensing cycle to create a higher quality beverage.
c) Displayed by the system for instant readout.
d) Used in other fashions.

In another embodiment of FIG. 1, when Controller 11 receives a signal to dispense beverage, Controller 11 opens Valve 6 and allows Water 3 to flow onto Sensor 9; the properties of the water are measured and communicated to Controller 11. The Controller 11 uses the water properties to provide a current calibration of the response of Sensor 9 to fluid properties; i.e., Controller 11 recalibrates Sensor 9. Controller 11 closes Valve 6 and opens Valves 4, and 5 to mix Fluids 1 and 2 in the Nozzle 7 in a set fashion (e.g., opening valve 4 while fluttering Valve 5) and dispense beverage into Cup 8. Part of the beverage is diverted and flows onto Sensor 9. The properties of the beverage are measured and sent to Controller 11. Because of the recalibration of Sensor 9 just prior to beverage dispensing, Controller 11 immediately uses the measured beverage properties in any of the following ways:

a) Sent to a data storage device (not shown) to inspection at a later time.
b) Used by the Controller 11 to adjust the dispensing of Fluids 1 and 2 during the next dispensing cycle to create a higher quality beverage.
c) Displayed by the system for instant readout.
d) Used in other fashions.

Both of these embodiments describe a beverage dispensing cycle that includes measuring properties of the beverage as well as measuring properties of water. The water measurement is used to calibrate the response of Sensor 9 and is immediately utilized to determine the quality of the beverage. Due to the short period of time between these two measurements, the possibility of erroneous readings (due to temperature changes of Sensor 9 or due to temperature changes of the beverage or due to fouling of Sensor 9 by the nature of the beverage) is greatly reduced. This represents an improvement over prior art.

Figure 2:
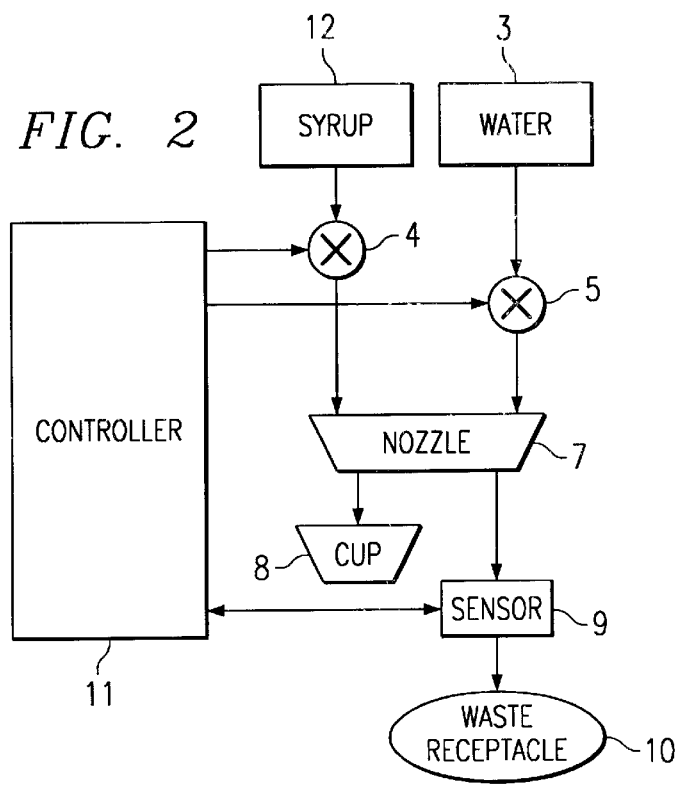
FIG. 2 depicts a block diagram of a system for sensing and controlling the quality of beverages where fluid #1 is a beverage concentrate or syrup and Fluid #2 is water.

Reference is now made to FIG. 2 which depicts a block diagram of a system for sensing and controlling the quality of a beverage which is the result of mixing of a beverage concentrate (or syrup) with water.

The system of the present invention includes a Controller 11 coupled with a plurality of electronically operated Valves 4 and 5 via electrical interfaces (not shown), as shown in FIG. 2. The system further includes Syrup 12 and Water 3 which are mixed in a Nozzle 7 to produce a beverage that is dispensed into Cup 8 for consumption. In this embodiment, Water 3 is utilized as both a known calibrating fluid as well as a component of the beverage. The system may also comprise a refrigeration system (not shown) for keeping the syrup and water chilled, and an ice dispenser (not shown).

The Electronic Controller 11 may be a microcontroller or digital signal processing (DSP) unit, such as TMS320F206 or TMS320F243, manufactured by Texas Instruments Incorporated of Dallas, Tex.

Sensor 9 is a fixed optical sensor, such as a surface plasmon resonance sensor, which is capable of determining some property of fluids, beverages, or water. Beverage (or water) is directed onto the sensor, properties are measured, and the beverage is directed into a Waste Receptacle 10.

During operation, Controller 11 is signaled to begin dispensing beverage. In one embodiment, Controller 11 causes Valves 4 and 5 to open in such a way as to mix Syrup 12 and Water 3 in the dispensing Nozzle 7 in a set fashion (e.g., opening Valve 5 while fluttering Valve 4). The resulting mixed beverage is dispensed into Cup 8 as well as a small portion is diverted onto Sensor 9; Sensor 9 measures the properties of the beverage and communicates these properties to Controller 11. Controller 11 retains the beverage properties. Immediately following this dispensing, Controller 11 closes valves 4 and leaves open Valve 5 which causes Water 3 to flow onto Sensor 9; the properties of the water are measured and are communicated to Controller 11. The Controller 11 closes Valve 5. The Controller 11 uses the measured properties of Water 3 to provide a current calibration of the response of Sensor 9 to fluid properties. The Controller 11 recalibrates Sensor 9 and adjusts the previous beverage measurement (which was retained by Controller 11) to determine the true quality of the beverage. The true quality of the beverage can be a) Sent to a data storage device (not shown) to inspection at a later time.
b) Used by the Controller 11 to adjust the dispensing of Syrup 12 and Water 3 during the next dispensing cycle to create a higher quality beverage.
c) Displayed by the system for instant readout.
d) Used in other fashions.

In another embodiment of FIG. 2, when Controller 11 receives a signal to dispense beverage Controller 11 opens Valve 5 and allows Water 3 to flow onto Sensor 9. The properties of Water 3 are measured and communicated to Controller 11. Controller 11 uses the water properties to provide a current calibration of the response of Sensor 9 to fluid properties. The Controller 11 recalibrates Sensor 9. Controller 11 opens Valve 1 (Valve 2 is left open) to mix Syrup 12 and Water 3 in the Nozzle 7 in a set fashion (e.g., opening Valve 5 while fluttering Valve 4) and dispense the mixed beverage into Cup 8. Part of the mixed beverage is diverted onto Sensor 9. The properties of the beverage are measured by Sensor 9 and sent to Controller 11. Because of the re-calibration of Sensor 9 just prior to beverage dispensing, Controller 11 immediately uses the measured beverage properties in any of the following ways:

a) Sent to a data storage device (not shown) to inspection at a later time.
b) Used by the Controller 11 to adjust the dispensing of Syrup 12 and Water 3 during the next dispensing cycle to create a higher quality beverage.
c) Displayed by the system for instant readout.
d) Used in other fashions.

Referring again to FIG. 2, a surface plasmon fixed optical sensor can be used to achieve precise ratios of syrup and water for consistently creating a beverage of a desired Brix value (sugar content) and quality. Surface plasmon resonance fixed optical sensors measure the refractive index of fluids which, in this case, can be related to the Brix value of a beverage. Prior to dispensing, zero-Brix water may be used to calibrate Sensor 9. In addition, a high quality soft drink from a bottle, for example, at a known level of Brix may be used to calibrate Sensor 9.

The present inventors found in practice however, that beverage temperature is not well controlled and can vary greatly (e.g., 3° C.–25° C.) both during dispenses and between dispenses. When this occurs, both the beverage temperature and the sensor temperature change unpredictably during operation. These unpredictable changes in beverage temperature and sensor temperature greatly affect the refractive index measurements, hence, the measured Brix value of the beverage leading to erroneous readings. The present inventors further found that natural products associated with beverages were capable of adhering to the surface of Sensor 9; this process is referred to as fouling of the sensor surface. Fouling can also lead to erroneous readings. These erroneous readings can prevent closed loop monitoring and system control from meeting desired specifications. Most preferably then, prior to each Sensor 9 reading, water (zero Brix) is drawn from Water Supply 3 via Valve 5 and passed over Sensor 9 in order to reference out any Sensor 9 temperature changes, and or any fluid temperature changes, and/or fouling of the Sensor 9. These techniques of continuous and multiple calibrations (during each and every dispense cycle), provide enhanced system calibration beyond that achievable, for example, simply by using water (or a high quality soft drink, from a bottle, for example, with a known level of Brix to calibrate Sensor 9 once for a long period time at a specific temperature (e.g., at the beginning of each day).

The desired Brix level of the dispensed beverage may be a predetermined default value stored in Controller 11, or alternatively, may be varied according to the operator's preference; enabling the operator to adjust the determined end point of quality or sweetness. Controller 11 may also be set to determining what level of quality or sweetness is deemed unacceptable; the unacceptable limits may also be set by the operator.

While this invention has been described with reference to illustrative embodiments, this description is not intended to be construed in a limiting sense. Various modifications and combinations of the illustrative embodiments as well as other embodiments of the invention will be apparent to persons skilled in the art upon reference to the description. It is therefore intended that the appended claims encompass any such modifications or embodiments.

What is claimed is:

1. A method of calibrating a beverage dispenser, comprising the steps of:

a) supplying a first fluid, wherein the flow of the first fluid is controlled by a first valve;
b) supplying a second fluid, wherein the flow of the second fluid is controlled by a second valve;
c) mixing the first fluid and the second fluid;

d) calibrating a fixed optic sensor via passing zero-Brix water, whose temperature is the same as that of the first and seconds fluids, onto the sensing surface of the fixed optic sensor such that temperature inaccuracies are referenced out and further such that contamination and fouling of the sensing surface by any fluids are substantially eliminated;

e) passing a sample of the mixture of the first fluid and the second fluid onto a sensing surface of the fixed optic sensor;

f) measuring one or more properties of the sample;

g) utilizing the measured properties to determine and improve the quality of the dispensed beverage; and h) repeating steps (a)–(g) until a desired ratio of fluid constituents is achieved.

2. The method as recited in claim 1 wherein the step of calibrating a fixed optic sensor comprises calibrating a surface plasmon resonance sensor.

3. The method as recited in claim 1 wherein the step of calibrating a fixed optic sensor comprises calibrating a refractometer.

4. The method as recited in claim 1 wherein the step of measuring one or more properties of the sample comprises measuring refractive index.

5. The method as recited in claim 1 wherein the step of supplying a first fluid comprises supplying water.

6. The method as recited in claim 1 wherein the step of supplying a second fluid comprises supplying concentrated flavored syrup.

7. The method as recited in claim 1 wherein the step of controlling the first valve based on the one or more properties comprises variably increasing and decreasing the diameter of the first valve.

8. The method as recited in claim 1 wherein the step of controlling the first valve based on the one or more properties comprises selectively opening and closing the first valve according to a prescribed first duty cycle.

9. The method as recited in claim 8 further comprising the step of adjusting the duty cycle of the first valve.

10. The method as recited in claim 1 further comprising the step of controlling the flow of the second fluid by a second valve.

11. The method as recited in claim 1 further comprising the step of triggering an alarm based on the one or more properties.

12. The method as recited in claim 1 further comprising the step of transmitting one or more data elements related to the one or more properties to a local data storage medium.

13. The method as recited in claim 1 further comprising the step of transmitting one or more data elements related to the one or more properties to a remote data storage medium.

14. The method as recited in claim 1 further comprising the step of determining when the supplying of the second fluid has ceased due to depletion of the second fluid.

15. The method as recited in claim 14 further comprising the step of supplying the second fluid from a different source from that which the depleted second fluid originated.

16. The method as recited in claim 1 further comprising the step of cleansing the sensing surface of the fixed optic sensor.

17. A method of calibrating a beverage dispenser having at least one fixed optic sensor and at least one fluid control valve, comprising the steps of:

a) calibrating the fixed optic sensor via passing zero-Brix water dispensed by the beverage dispenser onto the sensing surface of the fixed optic sensor such that temperature inaccuracies are referenced out;

b) passing a sample of a beverage having a plurality of constituents onto a sensing surface of the fixed optic sensor;

c) measuring at least one property of the sample;

d) adjusting the ratio of beverage constituents via the at least one fluid control valve based on the at least one property; and e) repeating steps (a)–(d) until a desired ratio of beverage constituents is achieved.

18. The method as recited in claim 17 wherein the step of calibrating the at least one fixed optic sensor comprises calibrating a surface plasmon resonance sensor.

19. The method as recited in claim 18 wherein the step of calibrating the at least one fixed optic sensor comprises calibrating a refractometer.

20. The method as recited in claim 17 wherein the step of measuring at least one property of the sample comprises measuring refractive index.

21. The method as recited in claim 17 wherein the step of adjusting the ratio of beverage constituents comprises adjusting a ratio of water and concentrated flavored syrup.

22. A method of calibrating a beverage dispenser having at least one fixed optic sensor and at least one fluid control valve responsive to measurements obtained via the at least one fixed optic sensor, comprising the steps of:

a) passing zero-Brix water having the same temperature as beverage, dispensed by the beverage dispenser, onto the sensing surface of the at least one fixed optic sensor; and b) calibrating the at least one fixed optic sensor in response to the zero-Brix water such that temperature inaccuracies associated with the at least one fixed optic sensor are referenced out.

23. The method as recited in claim 22 further comprising the steps of:

c) passing a sample of a beverage having a plurality of constituents onto a sensing surface of at least one fixed optic sensor;

d) measuring at least one property of the sample;

d) adjusting the ratio of beverage constituents via the at least one fluid control valve based on the at least one property; and e) repeating steps (a)–(d) until a desired ratio of beverage constituents is achieved.

24. The method as recited in claim 23 wherein the step of measuring at least one property of the sample comprises measuring refractive index.

25. The method as recited in claim 23 wherein the step of adjusting the ratio of beverage constituents comprises adjusting a ratio of water and concentrated flavored syrup.

26. The method as recited in claim 22 wherein the step of calibrating the at least one fixed optic sensor comprises calibrating a surface plasmon resonance sensor.

27. The method as recited in claim 22 wherein the step of calibrating the at least one fixed optic sensor comprises calibrating a refractometer.

* * * * *